(12) United States Patent
Szita et al.

(10) Patent No.: US 7,125,519 B1
(45) Date of Patent: Oct. 24, 2006

(54) ACTUATOR COUPLING SYSTEM AND A PIPETTING MODULE COMPRISING SUCH A COUPLING SYSTEM

(75) Inventors: Nicolas Szita, Cambridge, MA (US); Rudolf Buser, Grabs (CH); Olivier Elsenhans, Sins (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 777 days.

(21) Appl. No.: 10/148,149

(22) PCT Filed: Nov. 21, 2000

(86) PCT No.: PCT/EP00/11693

§ 371 (c)(1),
(2), (4) Date: May 23, 2002

(87) PCT Pub. No.: WO01/37996

PCT Pub. Date: May 31, 2001

(30) Foreign Application Priority Data

Nov. 26, 1999 (EP) .................................. 99811094

(51) Int. Cl.
*B01L 3/00* (2006.01)
(52) U.S. Cl. .................. 422/99; 422/100; 422/101; 422/102; 422/103; 422/112; 141/23; 141/242; 436/180
(58) Field of Classification Search ........... 417/360; 422/99–103, 112; 141/23, 242; 436/180
See application file for complete search history.

(56) References Cited

U.S. PATENT DOCUMENTS 4,303,376 A * 12/1981 Siekmann .............. 417/360
4,803,393 A    2/1989 Takahashi ............... 310/328
5,759,015 A    6/1998 Van Lintel et al. ......... 417/322
5,863,801 A    1/1999 Southgate et al. .......... 436/63
6,074,611 A    6/2000 Flesher .................... 422/100

FOREIGN PATENT DOCUMENTS

| DE | 43 13 370 A1 | 10/1993 |
| DE | 44 19 638 A1 | 12/1995 |
| EP | 0 865 824 A1 | 9/1998 |
| WO | 88/00708 | 1/1988 |
| WO | 97/15394 | 5/1997 |

\* cited by examiner

*Primary Examiner*—Jill Warden
*Assistant Examiner*—Jyoti Nagpaul
(74) *Attorney, Agent, or Firm*—McDonnell Boehnen Hulbert & Berghoff LLP

(57) ABSTRACT

The present invention is directed a system for coupling a macroactuator to a movable element of a micromachined device. The system includes a micromachined device, a first body for holding a macroactuator, a macroactuator mechanically mounted on the first body, a second body having a bore for receiving the first body, a screw arrangement for fixing the axial position of the first body within the bore of the second body, and a plate arrangement for mounting the micromachined device on the second body. The plate arrangement is mounted in such a way that the macroactuator exerts a predetermined force or pressure on a movable element of the micromachined device. The present invention further is directed to a pipetting module that includes the micromachined device and the macroactuator.

14 Claims, 12 Drawing Sheets

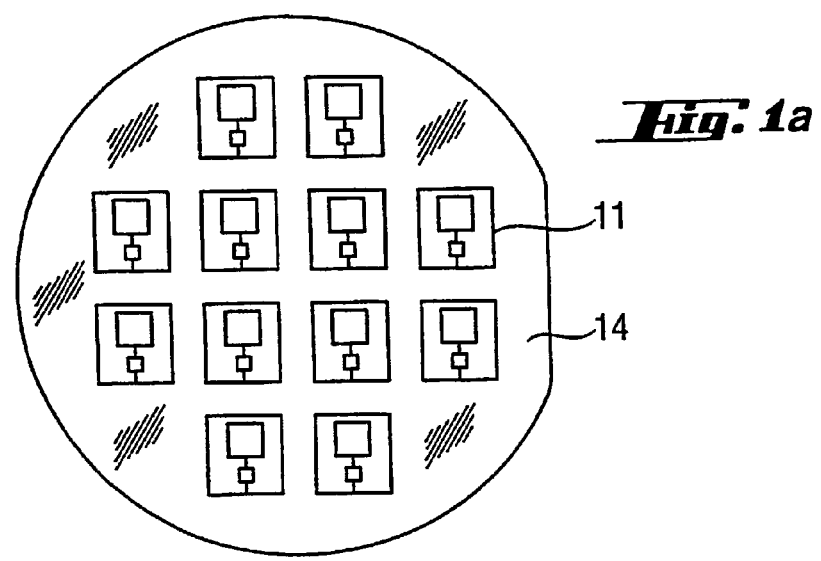
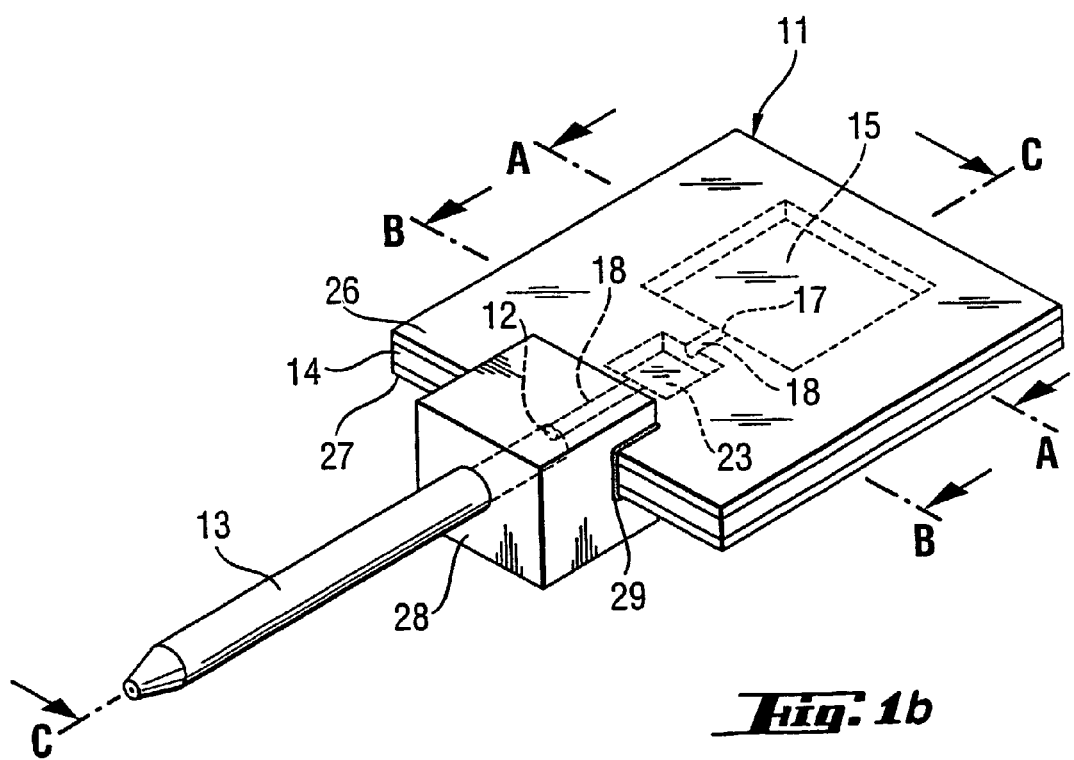

ACTUATOR COUPLING SYSTEM AND A PIPETTING MODULE COMPRISING SUCH A COUPLING SYSTEM

FIELD OF THE INVENTION

The invention concerns a system for coupling a macroactuator to a movable element of a micromachined device.

BACKGROUND OF THE INVENTION

Within the scope of the invention, a macroactuator is any actuator that cannot be manufactured by a micromachining process and which can therefore not be integrated in a micromachined device where an actuator is needed.

The invention also concerns a micropipetting module which comprises such a coupling system.

European Patent Application EP-A 0865824 A1 describes a micromachined pipetting device wherein a membrane is moved by means of a micromachined electrostatic actuator. With this kind of actuator it is difficult to produce forces which are sufficiently large as to displace the membrane with sufficient precision, in particular when the size of the membrane and the size of the necessary deflection of the membrane have to be increased in order to be able to increase the volume to be pipetted. With exception of thermal actuated micromechanical actuators, the strongest force that can be applied on the membrane with a micromechanical actuator is about one Newton. In order to overcome this limitation, it has been therefore proposed to use a macroactuator, e.g. a piezo-electric actuator, to effect the necessary deflection of the membrane of a micromachined pipetting device. Up to now a conventional approach proposed for this purpose has been to bond one end of the macroactuator to the membrane, e.g. by gluing that end to the membrane. Such a bonding is however disadvantageous, because it strongly limits flexibility of design of a pipetting module consisting of a micromachined pipetting device and a macroactuator connected thereto.

A first aim of the invention is to provide a system for coupling a macroactuator to a movable element of a micromachined device. The coupling system makes possible the positioning of the macroactuator with high precision with respect to the movable element and the transmission of the required large forces of a macroscopic actuator to that movable element for a precise and accurate large displacement thereof in order that that displacement can be effected with high accuracy and precision. Furthermore the coupling system should provide more flexibility for the overall design of a device which substantially consists of the micromachined device and of a macroactuator coupled thereto. A second aim of the invention is to provide a micropipetting module which comprises a coupling system according to the invention.

SUMMARY OF THE INVENTION

According to the invention the first aim is attained with a coupling system which comprises:

(a) a micromachined device having a movable element, (b) a first body for holding a macroactuator, said first body having a side wall having an outer surface and a bottom having an outer surface, (c) a macroactuator which has an upper end and a lower end, and which is mechanically mounted on said first body, (d) a second body having an upper outer surface, a lower outer surface, and a bore for receiving said first body, the size of said bore and the size of said first body being such that the outer surface of the sidewall of the first body snugly fits within said bore, (e) means for fixing the axial position of said first body within said bore, and (f) means for mounting said micromachined device on said second body in such a way that the upper end of the macroactuator exerts a predetermined force or pressure on said movable element of said micromachined device.

According to the invention, the second aim is attained with a pipetting module which comprises:

(a) a micromachined pipetting device for pipetting liquid volumes in the submicroliter and microliter range, said micromachined pipetting device including a membrane having a central zone, the central zone of said membrane being displaced by a macro actuator, (b) a macroactuator for displacing said membrane, and (c) means for mechanically coupling said macroactuator to said membrane of said micromachined pipetting device.

Preferred embodiments of the invention have the features defined by the dependent claims.

The advantages obtained with a coupling system according to the invention are as follows:

A coupling system according to the invention enables coupling of a macroactuator (macroscopic actuator) to a micromachined device.

The position of the macroactuator with respect to the micromachined device is adjustable (before use thereof) with high precision (with a tolerance or clearance of ±1 micrometer or even less than ±1 micrometer) and on a relatively wide range. The position of the macroactuator towards the micromachined device can be adjusted to the micrometer with an appropriate measurement system (e.g. laser measurement of the membrane deflection) and is thus precise enough for micro-system applications.

A practically shift-free fixation of the macroactuator with respect to the micromachined device is achieved.

A shift-free position of the macroactuator with respect to the micromachined device is maintained during operation, even when the macroactuator exerts relatively large forces on the movable element of the micromachined device, or when large forces are imposed on the coupling system as a whole.

A bond-free coupling of the macroactuator to the movable element, e.g. a membrane, of the micromachined device is achieved.

The latter bond-free coupling provides the following further advantages:

In the case where the micromachined device is a micropipetting device having a membrane as a movable element, the strength of the relaxation force of the membrane can be adjusted by optimizing the position of the macroactuator with respect to the micromachined device. The optimized position of the macroactuator is optimized between the strong deformation force of the actuator and the increasing relaxation force of the membrane. For maximum displacement of the membrane and for maximum relaxation force and large deflection of the membrane, the membrane may be made of monocrystalline silicon (m-silicon).

The modular set-up of the actuation coupling system according to the invention provides a high degree of flexibility for choosing the required displacement of, and force exerted on, the membrane of the micropipetting device. This modular set up makes possible to adapt either the membrane of the micropipetting device or the actuator type. Changing of the geometry of the membrane or the parameters of the actuator opens up a wide range of possible performance parameters of the complete device, i.e. a wide range of volumes to be displaced, a wide range of force applicable to the membrane, etc.

The modular set-up of the pipetting module according to the invention provides a high degree of flexibility for choosing the micromachined pipetting device and the macroactuator to be coupled thereto.

BRIEF DESCRIPTION OF THE DRAWINGS

Examples of embodiments of the invention are described hereinafter with reference to the accompanying drawings wherein:

FIG. 1a is a schematic view of an array of micromechanical modules formed on a silicon wafer, which modules are apt to be used as a component of a micromechanical pipetting device.

FIG. 1b is a schematic view of a micromechanical pipetting device built with one of the micromechanical modules of the array shown by FIG. 1a.

FIG. 10 illustrates the positioning of inner cylinder 51 in the bore of outer cylinder 61 by means of the additional components of coupling components shown by the lower half of FIG. 9.

DETAILED DESCRIPTION OF THE INVENTION

Micromechanical Pipetting Device

Figure 2:
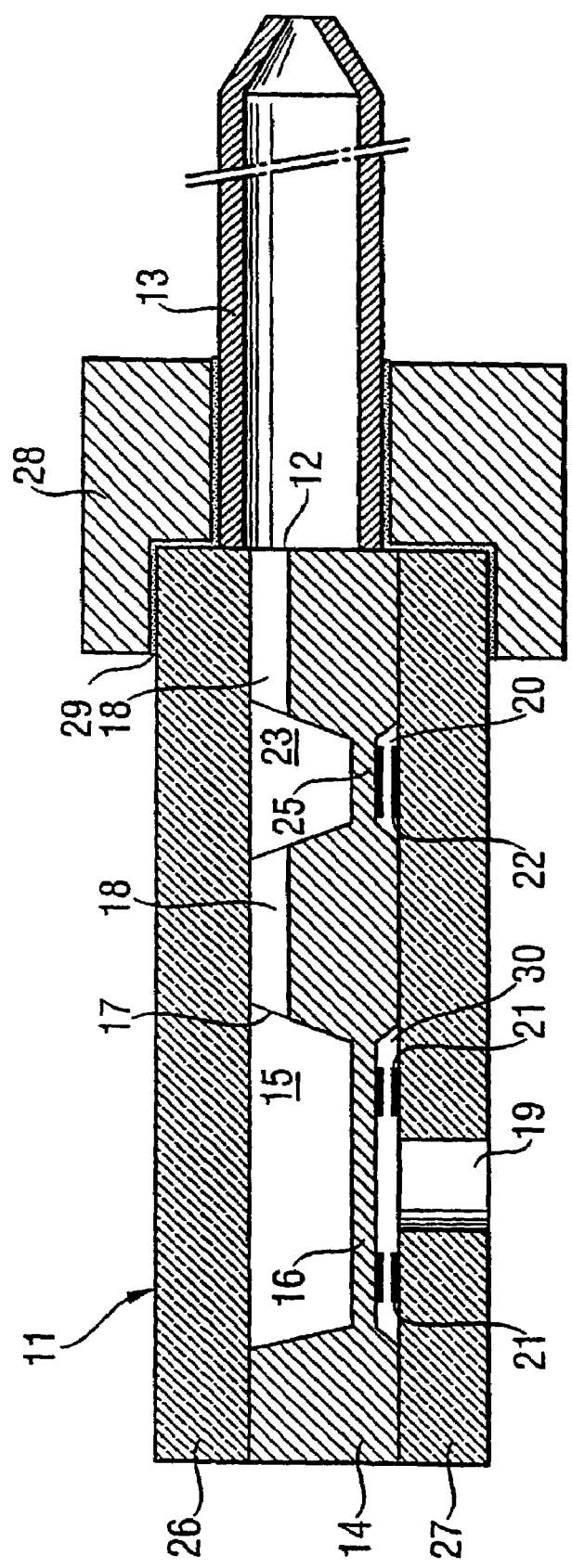
FIG. 2 is a representation of a longitudinal cross-section on the line C—C in FIG. 1b.

FIG. 1a shows schematically a silicon wafer 14 on which an array of micromechanical modules has been formed. Each of such modules can be used as a component of a micromechanical pipetting device 11.

FIG. 1b shows schematically a micromechanical pipetting device 11. Liquid volumes in the submicroliter and microliter range can be pipetted with such a device. Device 11 is an integrally built pipetting device comprising a micromechanical structure which is integrally built on a silicon wafer 14.

The micromechanical pipetting device 11 shown by FIG. 1b comprises three layers arranged one above the other and connected to one another unreleasably by means of anodic bonding or other bonding process e.g. silicon direct bonding as follows: a first glass or silicon layer 26, a second glass or silicon layer 27, and a silicon wafer layer 14 arranged between layers 26 and 27. Silicon wafer layer 14 is unreleasably connected to layers 26 and 27 by means of one of the above mentioned bonding processes. Silicon wafer layer 14 in FIG. 1b has a surface of approximately 25×10 mm$^2$ for the smaller volumes of the target range (submicroliter or microliter range).

Silicon wafer layer 14 comprises a chamber 15 and a channel 18 formed by micromachining on wafer 14. The bottom wall of chamber 15 is a membrane 16. Chamber 15 has one opening 17 which is connected to one end of channel 18. The opposite end of channel 18 forms an inlet/outlet 12 of pipetting device 11. A pipetting tip 13 is connected to inlet/outlet 12 by means of a connecting element 28 and a sealing film 29. Connecting element 28 is made e.g. of a plastic material called PMMA (polymethylmethacrylate).

FIG. 2 shows a longitudinal section on the line C—C in FIG. 1b. As shown by FIG. 2, a micromechanical pipetting device 11 shown by FIG. 1b comprises chamber 15 having membrane 16 as a bottom wall, channel 18, a bore 19 in glass or silicon layer 27, this bore 19 providing access for an actuator means for displacing membrane 16, and sensor means 21 for generating an output signal related to the displacement of the membrane 16. A portion of the membrane 16 is part of the sensor means 21 and the output signal generated by this sensor means is representative of the displacement of the membrane 16.

Sensor 21 is preferably an electrode of a displacement sensor. Sensor 21 in FIG. 2 is a displacement sensor comprising an electrical capacitor as a measuring element. Sensor 21 in FIG. 2 can be replaced by an electro-optical sensor.

Micromechanical pipetting device 11 further comprises a chamber 23 formed by a portion of channel 18, and sensor means 22 for generating a further output signal related to the displacement of the membrane 16. The bottom wall of chamber 23 is a sensor membrane 25. A portion of channel 18 is part of sensor means 22.

Sensor 22 is for instance an electrode of a pressure sensor or a flow measurement sensor. Sensor 22 in FIG. 2 is pressure sensor comprising an electrical capacitor as a measuring element. Sensor 22 can also be a piezoresistive sensor.

The volume comprised within chamber 15 is apt to be modified by displacement of the membrane 16. Chamber 15 has only one opening 17 which is permanently open and which allows fluid flow into and from the interior of chamber 15.

Channel 18 establishes a direct, valveless and permanent fluidical connection between opening 17 of chamber 15 and the inlet/outlet 12 of the pipetting device 11.

Figure 3:
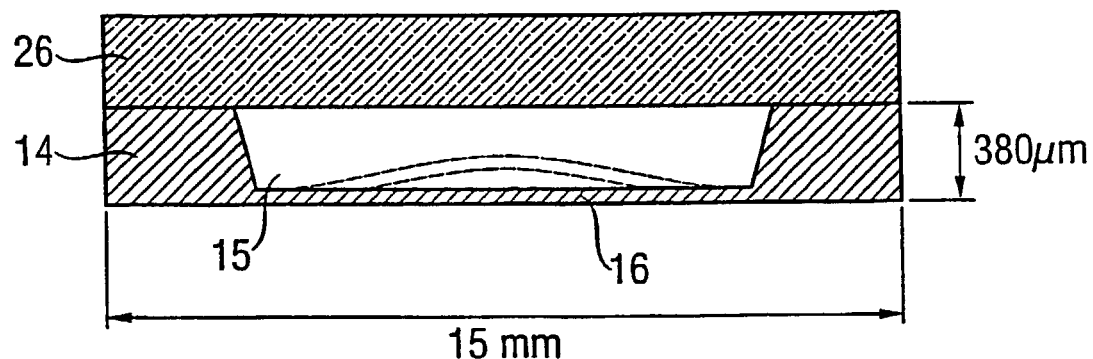
FIG. 3 is a partial representation of a cross-section on the line A—A in FIG. 1b.

FIG. 3 shows a partial representation of a cross-section on the line A—A in FIG. 1b. FIG. 3 shows in particular the cross-sectional shape of chamber 15 and an example of the width and depth of wafer layer 14 of pipetting device 11. The broken line in FIG. 2 shows the position taken by the membrane 16 when it is displaced e.g. by means of an actuator located below membrane 16, but not represented in FIG. 2.

Figure 4:
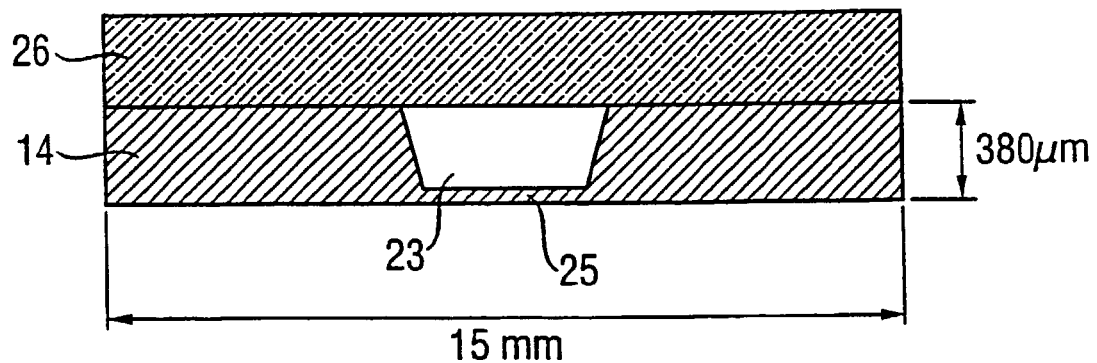
FIG. 4 is a partial representation of a cross-section on the line B—B in FIG. 1b.

FIG. 4 shows a partial representation of a cross-section on the line B—B in FIG. 1b. FIG. 4 shows in particular the cross-sectional shape of chamber 23 of device 11.

Figure 5:
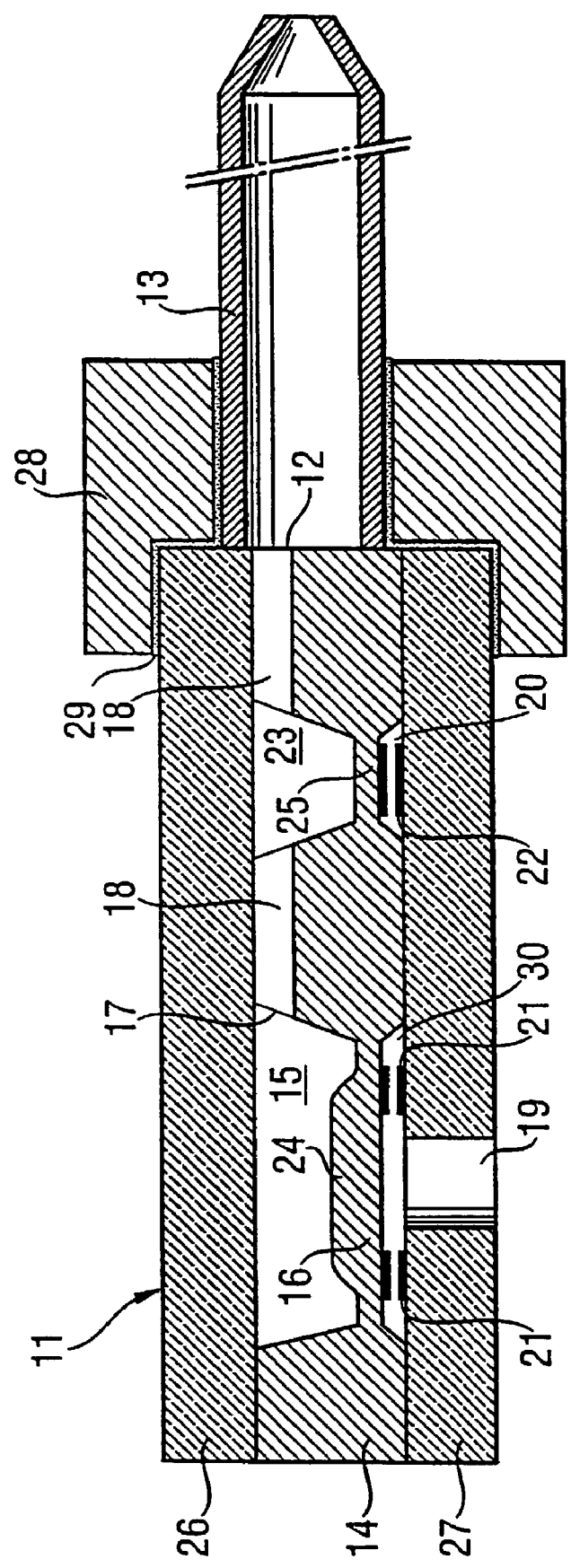
FIG. 5 is a representation of a longitudinal cross-section of a preferred embodiment, which is similar to the embodiment shown in FIG. 1b, but wherein membrane 16 has a boss 24.

FIG. 5 is a representation of a longitudinal cross-section of a preferred embodiment which is similar to the embodiment shown in FIG. 1b, but wherein membrane 16 has a boss 24.

In order to perform a pipetting operation with the pipetting device 11, actuator means are activated to displace membrane 16 for aspiring or expelling a volume of air or of a liquid into or from chamber 15. Such a displacement of membrane 16 causes a corresponding aspiring or expelling of a volume of a liquid sample into or from respectively said pipetting tip 13.

When a pipetting device 11 is used to perform pipetting operations, the interior of the pipetting device is filled either with air or with a system liquid (e.g. water) separated from the pipetted liquid by an air segment. Sample or reagent is aspired or expelled from the pipetting tip when actuator 19 displaces membrane 16. While pipetting, the pipetted liquid (for instance a biological liquid sample or a reagent for performing a clinical chemistry test) does not enter channel 18 but remains within the pipetting tip.

Coupling System According to the Invention

Figure 6:
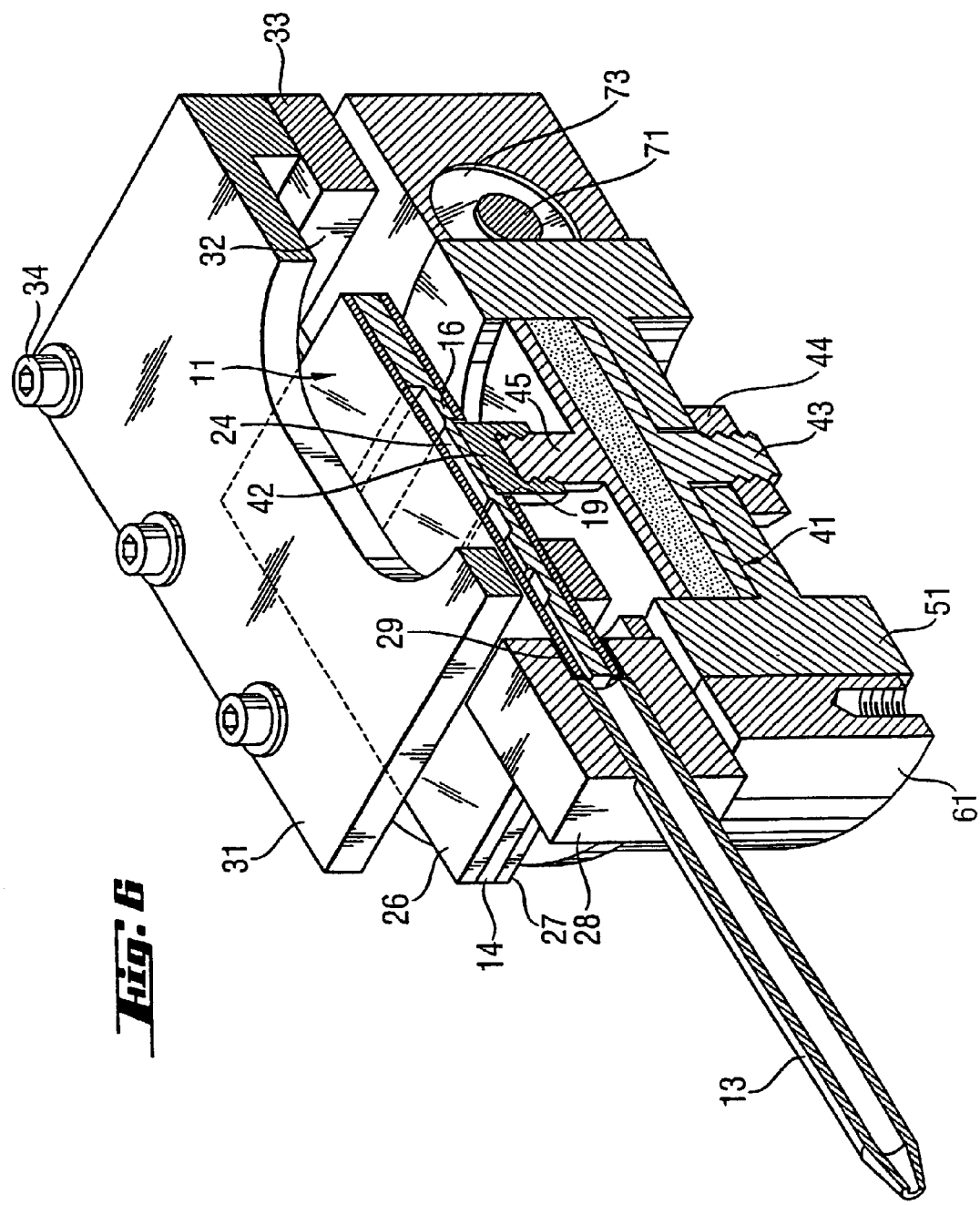
FIG. 6 shows a schematic perspective view of an embodiment of a system according to the invention for mechanically coupling an actuator 41 to the membrane 16 of a micromechanical pipetting device 11 of the type shown by FIGS. 1–5.
Figure 7:
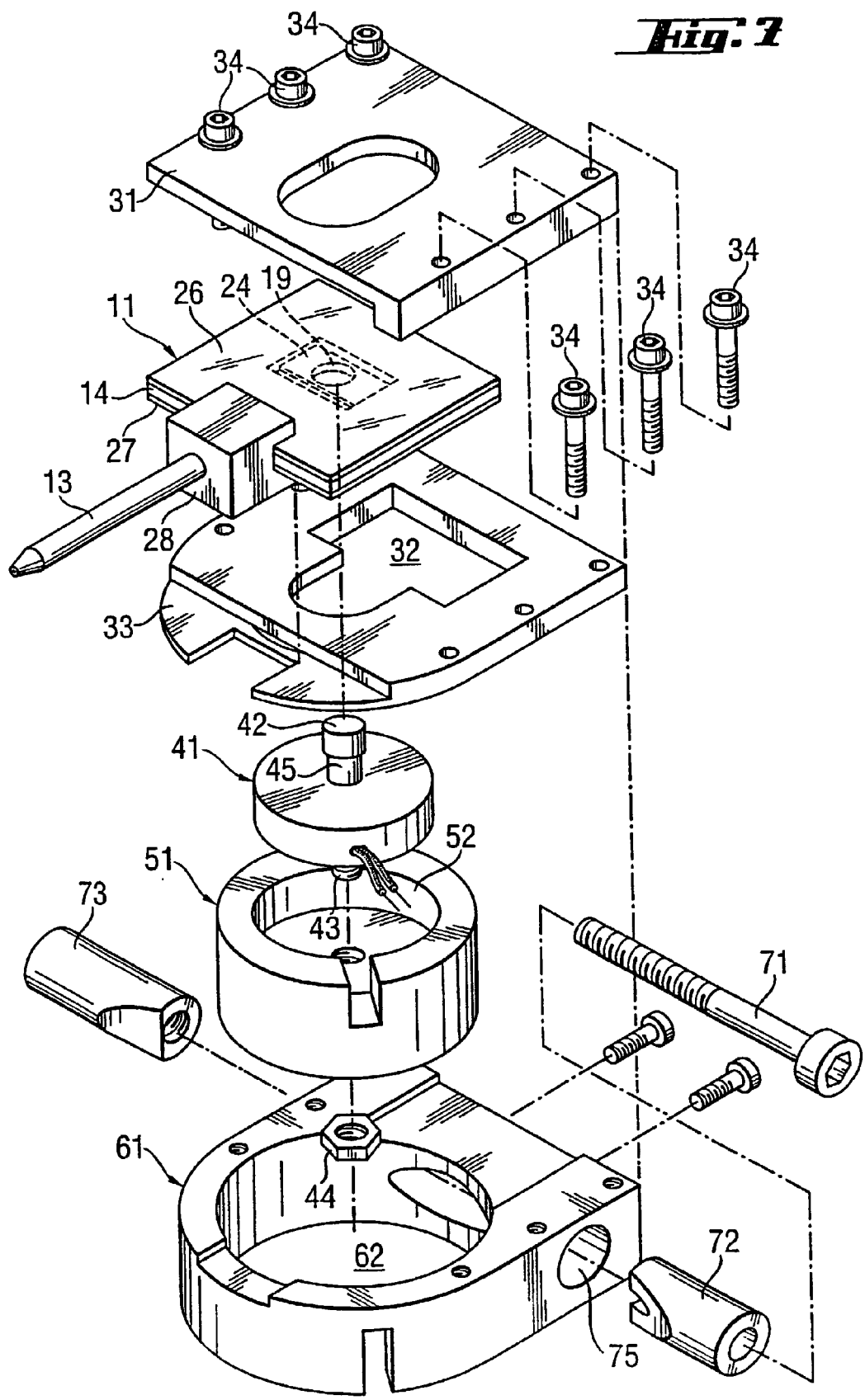
FIG. 7 shows an exploded view of the components shown by FIG. 6.

FIG. 6 shows a schematic perspective view of an embodiment of a system according to the invention for mechanically coupling a macroactuator 41, e.g. a piezo disk translator or any other type of macroactuator, to a movable element of a micromachined device, e.g. to the membrane 16 of a micromechanical pipetting device 11 of the type shown by FIGS. 1–5. FIG. 7 shows an exploded view of the components shown by FIG. 6.

As can be appreciated from FIGS. 6 and 7, a coupling system according to the invention comprises the following components:

(a) A micromachined device having a movable element. The micromachined device is e.g. a micromachined pipetting device 11 of the type described above with reference to FIGS. 1–5 and has a membrane 16 as a movable element. Micromachined pipetting device 11 is e.g. configured and dimensioned for enabling pipetting of liquid volumes in a range between a minimum value smaller than a microliter and a maximum value of about 10 microliters. The central zone of the membrane 16 is adapted to be displaced by a macroactuator.

(b) A first body (51) adapted for holding a macroactuator, said first body (51) having a side wall having an outer surface and a bottom having an outer surface.

(c) A macroactuator 41 which has an upper end 45 and a lower end 43, and which is mechanically mounted on said first body 51. In the embodiments shown in FIGS. 6, 7, 9, 10, a cap 42 is screwed on top of the upper end 45 of macroactuator 41. The purpose of this cap is to protect the membrane from contact with sharp edges of the tip of upper end 45 of macroactuator 41. Cap 42 can however be eliminated if the latter tip has a shape without any sharp edge that may damage membrane 16. A nut 44 is provided on the lower end 43.

(d) A second body 61 having an upper outer surface, a lower outer surface, and a bore 62 for receiving first body 51, the size of said bore 62 and the size of said first body 51 being such that the outer surface of the first body 51 snugly fits within said bore 62.

(e) Means 71, 72, 73, 75 for fixing the axial position of said first body 51 within said bore 62 (also referred to as a screw arrangement for fixing).

(f) Means for mounting said micromachined device 11 on said second body 61 in such a way that the upper end 45 of the actuator exerts a predetermined force or pressure on said movable element of said micromachined device 11 (also referred to as a plate arrangement for mounting).

In a preferred embodiment, first body (51) has a substantially cylindrical shape, comprises a chamber (52) for receiving macroactuator 41, and a substantial part of macroactuator (41) is located in chamber (52) of first body (51).

Within the scope of the invention, macroactuator 41 is any actuator which cannot be manufactured by a micromachining process and which is apt to exert on membrane 16 a force larger than one Newton and along a displacement of the membrane of about 10 micrometers or more.

Figure 8A:
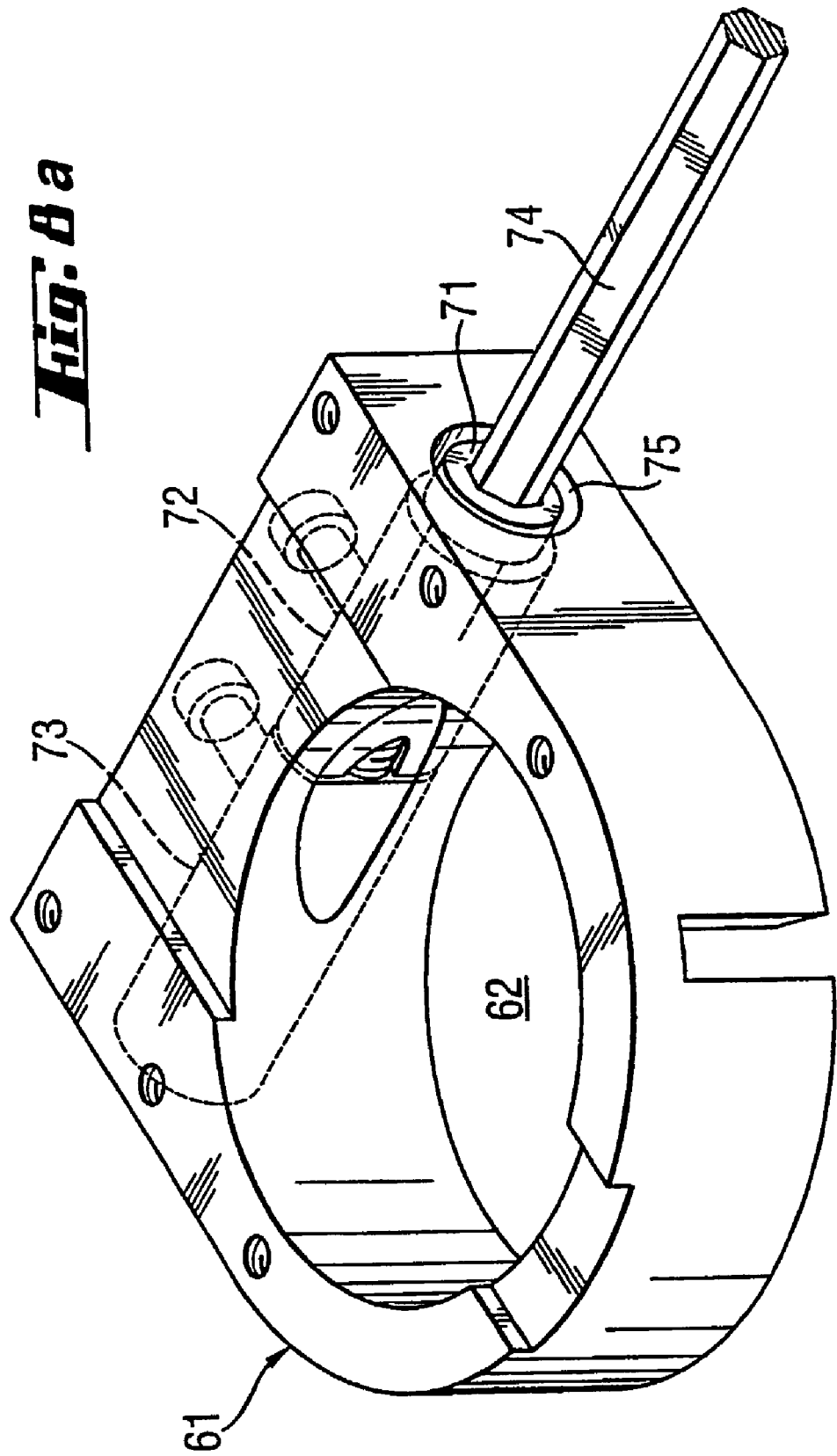
FIG. 8a shows outer cylinder 61 shown in FIGS. 6–7. This Figure shows in particular how bolt segments 72 and 73 are moved against each other by turning screw 71 with a screw driver 74.
Figure 8B:
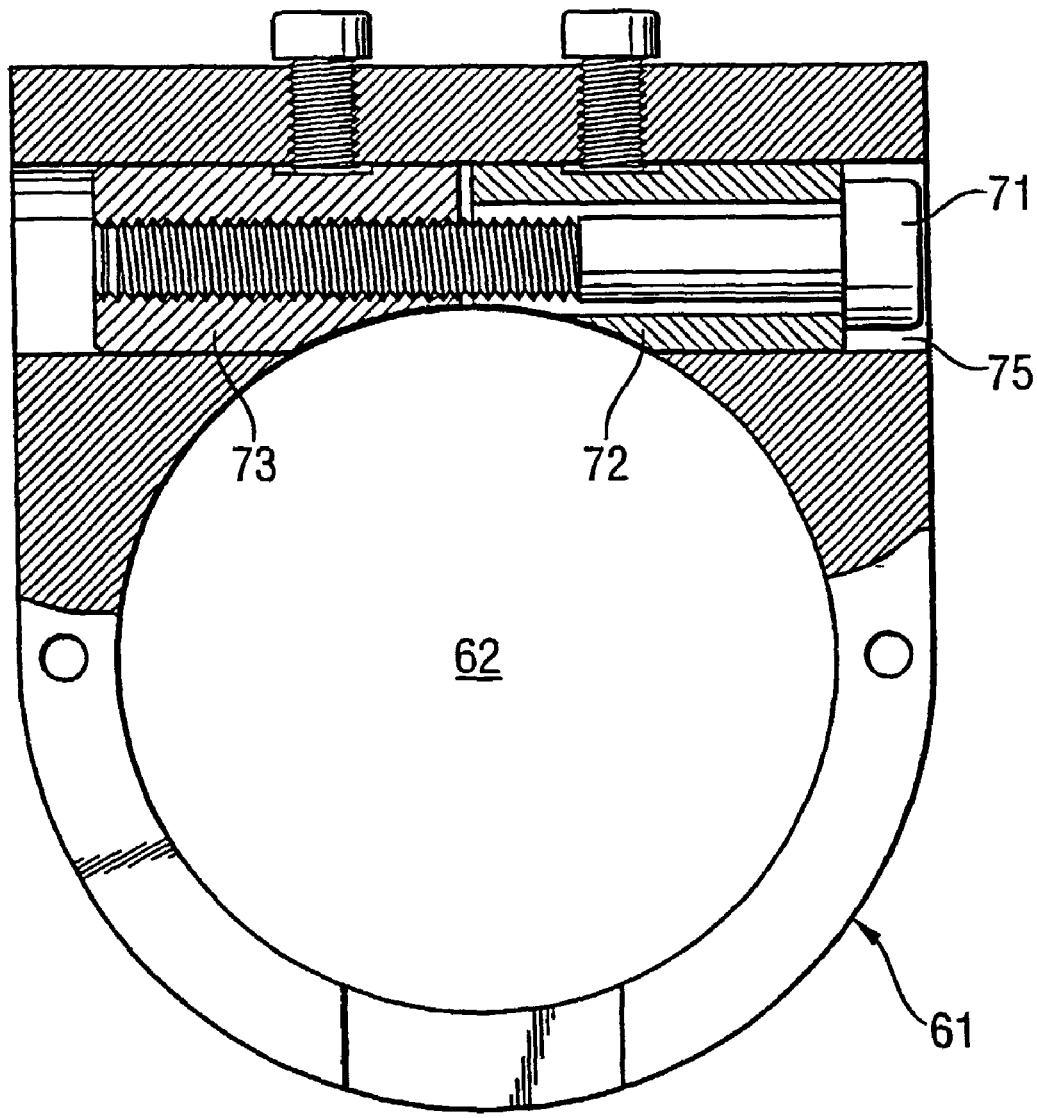
FIG. 8b shows a cross-section of the embodiment shown by FIG. 8a in a plane which is normal to the length axis of bore 75.

As can be appreciated in particular from FIGS. 8a and 8b, the means for fixing the axial position of said first body 51 within said bore 62 of second body 61 comprise a first bolt segment 72 and a second bolt segment 73. These bolt segments 72, 73 are located within a bore 75 of second body 61. Each of bolt segments 72, 73 has a side wall which has the same radius of curvature as a closed line defined by a cross-section of bore 62 of second body 61. In a preferred embodiment, said closed line is a circle. The means for fixing the axial position of said first body 51 within said bore 62 of second body 61 further comprise a screw 71 passing through bolt segment 72 and being connectable to bolt segment 73 by a screw connection. The screw connection is adapted to enable bolt segments 72, 73 to be pulled against each other by turning screw 71 with a screw driver 74 in order to reduce an initial gap existing between bolt segment 72 and bolt segment 73 and thereby reduce the space available for said first body 51 in bore 62 of second body 61.

A further embodiment of a coupling system according to the invention is described hereinafter with reference to FIGS. 9 and 10. This embodiment is based on the embodiment described above with reference to FIG. 6 and comprises additional means for adjusting with high accuracy the axial position of first body 51 in bore 62 of second body 61 (also referred to as an arrangement for adjusting).

Figure 9:
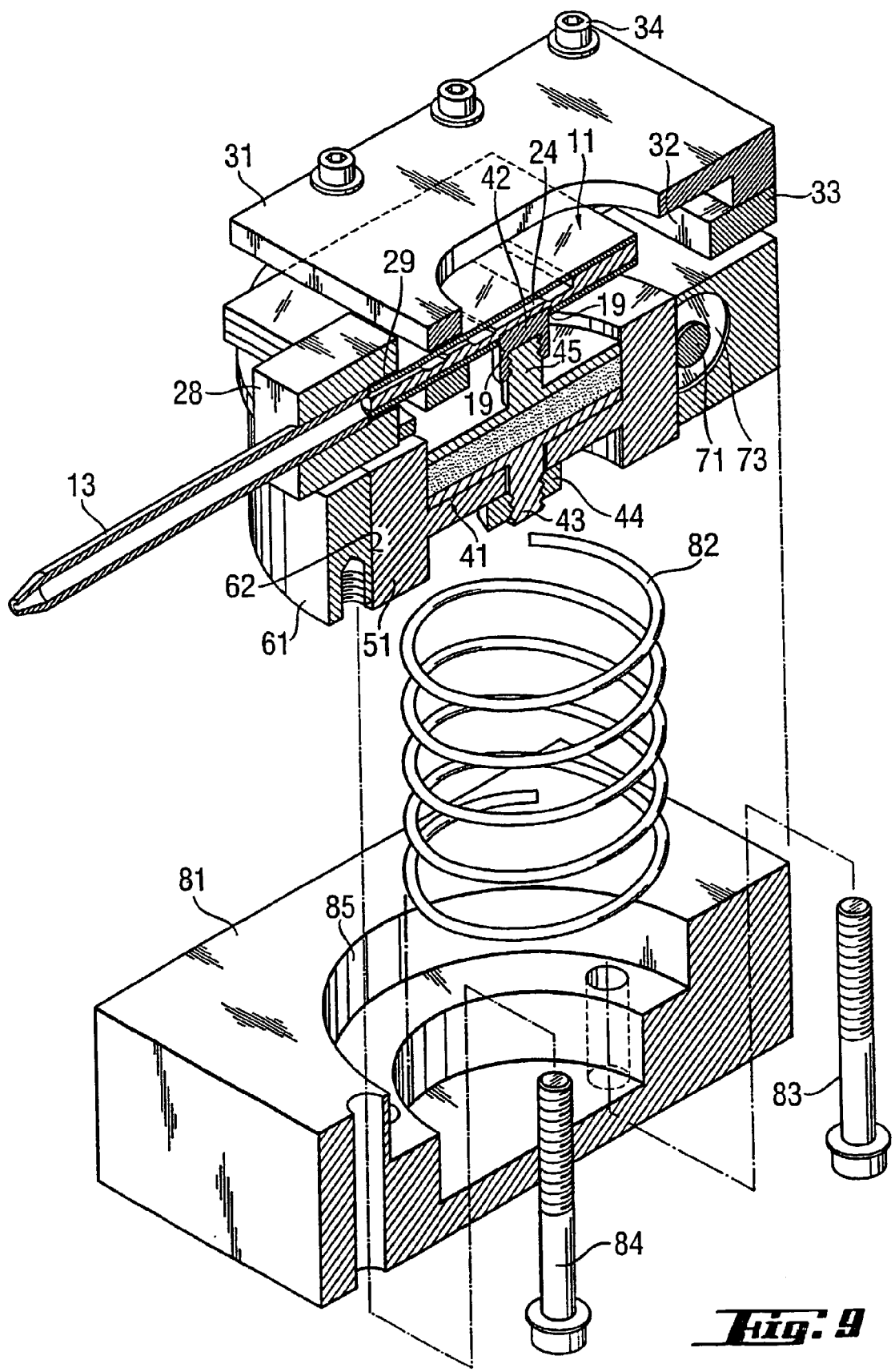
FIG. 9 schematically shows a schematic perspective view of the embodiment shown by FIG. 6 and an exploded view of additional components of coupling means used for fixing with high precision the position of inner cylinder 51 in the bore 62 of outer cylinder 61.

FIG. 9 schematically shows a schematic perspective view of the embodiment shown by FIG. 6 and an exploded view of additional components of coupling means used for fixing with high precision the position of inner cylinder 51 in the bore 62 of outer cylinder 61. FIG. 10 shows a cross-sectional view of the embodiment shown by FIG. 9 when the components shown therein are assembled. FIG. 10 illustrates the positioning of inner cylinder 51 in the bore of outer cylinder 61 by means of the additional components of coupling components shown by the lower half of FIG. 9.

Figure 10:
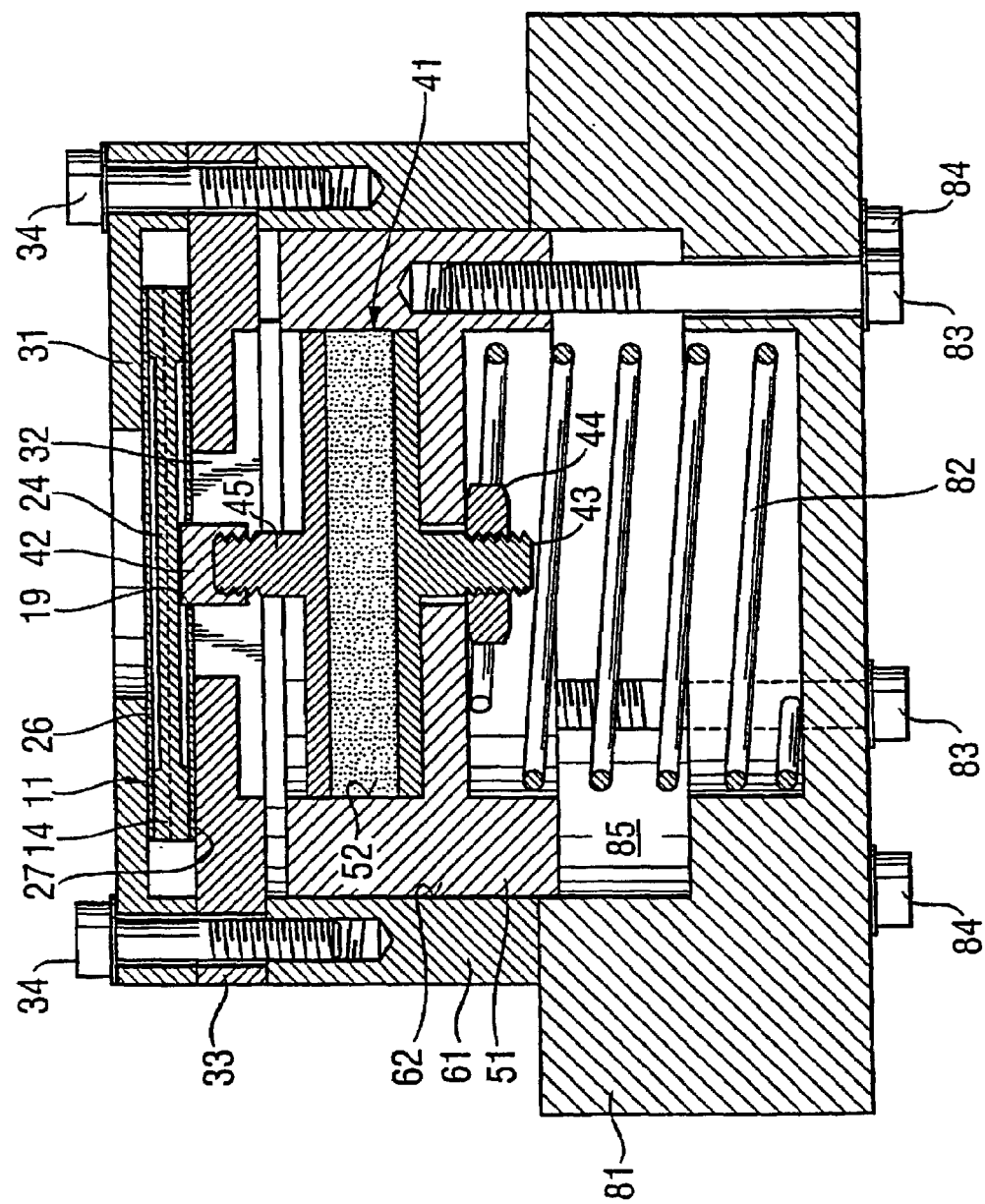
FIG. 10 shows a cross-sectional view of the embodiment shown by FIG. 9 when the components shown therein are assembled.

The additional components of the embodiment according to FIGS. 9 and 10 are as follows:

(g) A basis plate 81 which is adapted to be removably mechanically connected to first body 51 and to second body 61. Basis plate 81 has an upper outer surface and a cavity 85 adapted to receive a lower part of said first body 51. Cavity 85 extends towards a bottom wall of basis plate 81 and this bottom wall has an inner surface.

(h) First connecting means, e.g. screws 84, for mechanically connecting second body 61 to basis plate 81 so that the lower outer surface of second body 61 contacts the upper outer surface of basis plate 81.

(j) Spring means 82 which are adapted to be inserted between basis plate 81 and first body 51 in such a way that when second body 61 is connected to basis plate 81, the spring means 82 exert a force on said first body 51 and that force pushes first body 51 upwards through bore 62 of second body 61.

(k) Second connecting means, e.g. screws 83, for mechanically connecting first body 51 to basis plate 81 in such a way that the distance between the outer surface of the bottom of first body 51 and the inner surface of the bottom wall of basis plate 81 is adjustable within a certain range. The function of the second connecting means 83 is to exert on first body 51 a force opposite to the force exerted thereon by spring means 82.

Figure 12:
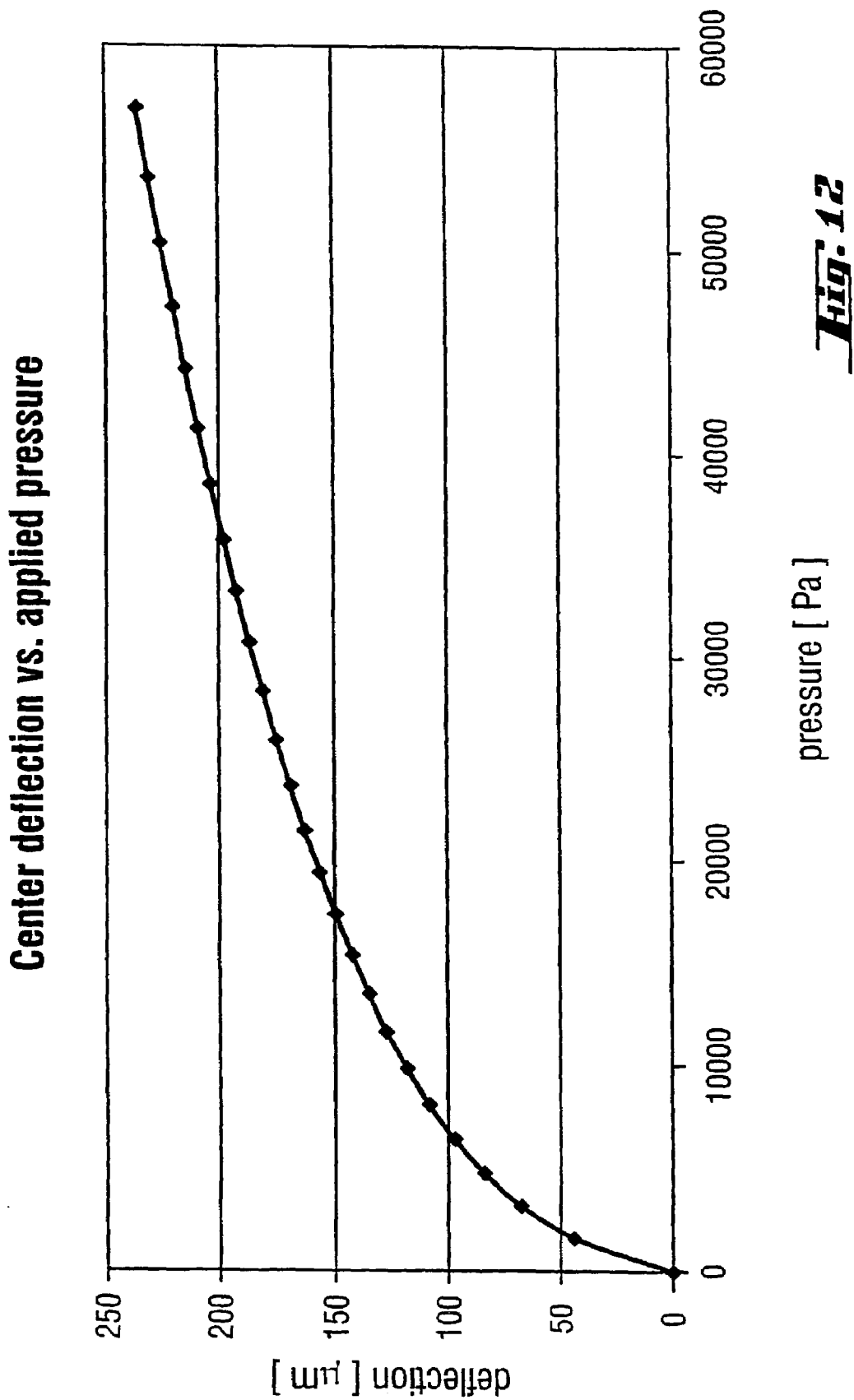
FIG. 12 shows a diagram of deflection of the center of a membrane of a micromechanical pipetting device versus pressure exerted on the membrane for causing said deflection of the membrane.

A typical diagram of deflection of the center of a membrane of a micromechanical pipetting device versus pressure exerted on the membrane for causing said deflection is represented in FIG. 12.

The advantages provided by a coupling system according to the invention in the case where the micromachined device is e.g. a micropipetting device 11 of the kind described with reference to FIGS. 1–5 will be better understood by noting that when micropipetting device 11 has a large m-silicon membrane the following facts apply:

A large mono-crystalline (m-silicon) silicon membrane permits large deflections. The relaxation forces thereby increase progressively, i.e. the membrane behaves like a progressive spring with an over-proportional increase (that is with a proportionality factor larger than one) of the relaxation forces versus the deformation. Therefore, depending on the position of the actuator towards the actuator membrane, within the scope of the invention a different membrane pre-load is chosen. This offers the possibility to adjust the strength of the relaxation force over the actuation stroke, hence permitting the finding of an optimized position for maximum membrane displacement and maximum membrane force, said optimized position being optimized between strong deformation force of the actuator and increasing relaxation force of the membrane.

Pipetting Module According to the Invention

A particularly advantageous application of a coupling system according to the invention is the use of such a system as part of a pipetting module which is e.g. suitable as a component of a pipetting unit of an automatic analyzer for the analysis of liquid biological samples. Such a pipetting module comprises according to the invention the following components shown by FIGS. 6 and 7:

(a) A micromachined pipetting device 11 for pipetting liquid volumes in a range between a minimum value smaller than a microliter and a maximum value of about 10 microliters. Micromachined pipetting device 11 includes a membrane 16, the central zone of which is adapted to be displaced by a macroactuator, (b) A macroactuator 41 adapted to effect a displacement of membrane 16.

(c) Means for mechanically coupling macroactuator 41 to membrane 16 of micromachined pipetting device 11.

Micromachined pipetting device 11 is e.g. as described above with reference to FIGS. 1 to 5. Therefore, micromachined pipetting device 11 includes a membrane 16 formed by a silicon layer 14 arranged between an upper glass or silicon layer 26 and a lower glass or silicon layer 27, said lower glass or silicon layer 27 has a bore 19 which provides said macroactuator 41 access to the central part of said membrane 16.

In a preferred embodiment, membrane 16 has a boss 24 in its central part. The advantage provided by the presence of boss 24 at the point of contact is that it ensures an optimum transmission of the actuation stroke and power.

The means for mechanically coupling macroactuator 41 to membrane 16 are e.g. as described above with reference to FIGS. 6 to 10.

A preferred embodiment of the means for mechanically coupling macroactuator 41 to membrane 16 further comprise means for mounting micromachined pipetting device 11 on second body 61, and the latter means comprise e.g. the following components:

(i) A clamping plate 31 which covers the micromachined pipetting device 11.

(ii) A mounting plate 33 which is located below the micromachined pipetting device 11 and which has a window 32 that provides access to bore 19 of the lower glass or silicon 27.

In this preferred embodiment, the micromachined pipetting device 11 is arranged between clamping plate 31 and mounting plate 33 and is mounted with these plates on second body 61 e.g. by means of screws 34.

A pipetting operation carried out with a pipetting device comprising the above described coupling system is described hereinafter for the case in which the membrane 16 has a boss 24 is basically as follows:

The deflection of membrane 16 is effected with the coupled macroactuator 41. The actuator stroke on the membrane boss 24 determines the membrane deflection, hence the displaced volume. For the dispensing part of the operation, the displacement of membrane 16 is actively pushed by macroactuator 41. For the aspiration part of the operation, the relaxation forces of membrane 16 itself pull the membrane back to the initial position thereof determined by the actuator position. It is thus a passive actuation procedure.

As already mentioned above, within the scope of the invention, macroactuator 41 is any actuator which cannot be manufactured by a micromachining process and which is apt to exert on membrane 16 a force of at least one Newton and this along a membrane displacement of 10 micrometers or more. This capability of macroactuator 41 is advantageous in particular when the pipetting tip of micromechanical pipetting module 11 is relatively long and/or when the volume to be pipetted is relatively large.

Figure 11:
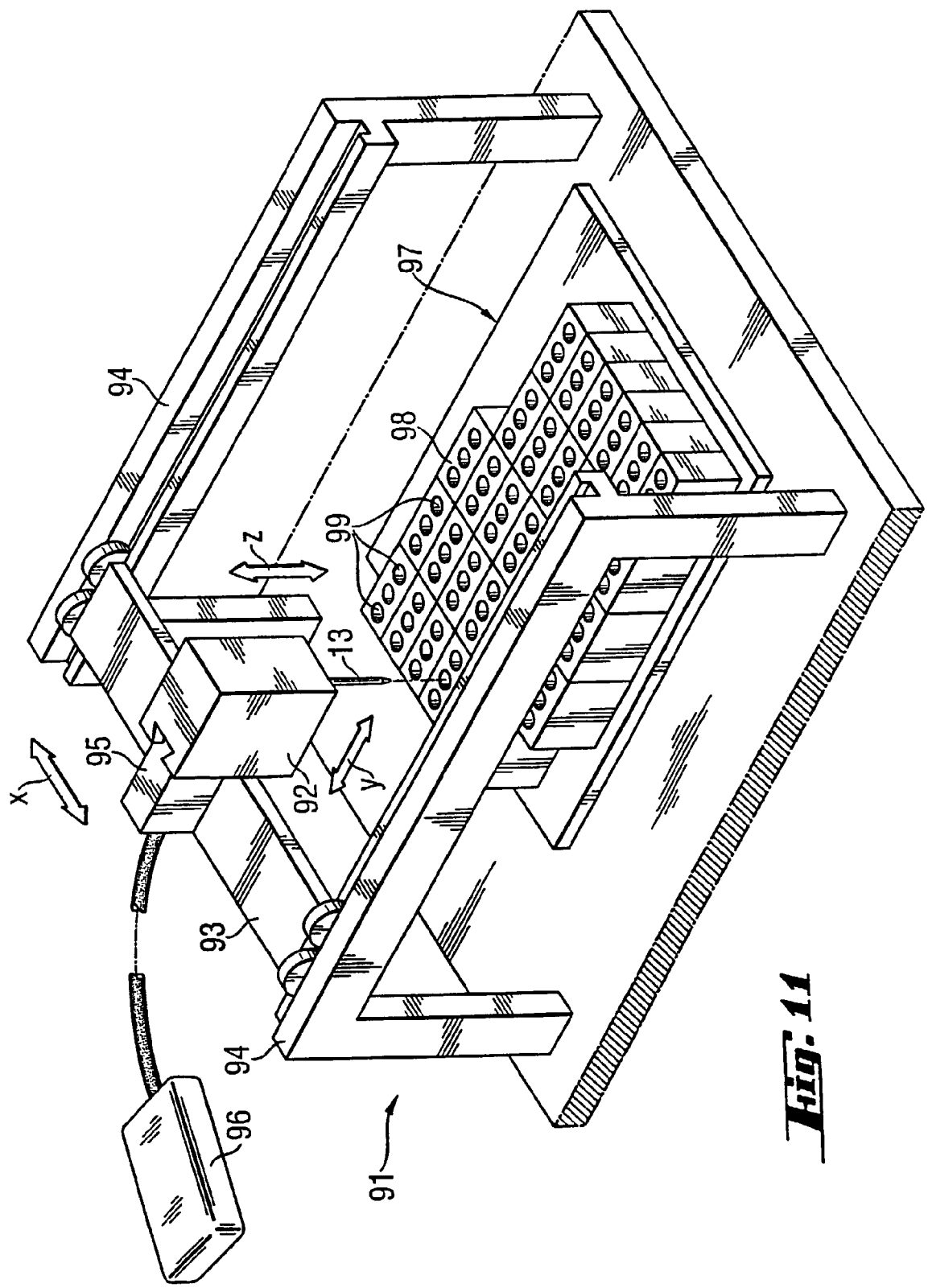
FIG. 11 shows a part of a pipetting unit including a micromechanical pipetting device of the type shown by FIGS. 6 to 8.

FIG. 11 shows a part of a pipetting unit including a pipetting module of the type described above and suitable for pipetting of biological liquids in the micro- and submicroliter range, in particular for industrial use in a commercial in-vitro diagnostics.

In the pipetting unit shown by FIG. 11, a pipetting head 92 contains a pipetting module of the type described above and has a pipetting tip or needle 13. Pipetting head 92 is moved by means of a transport system 91 in three orthogonal directions X, Y, Z. Transport system 91 includes a transport bar 93 for transport in X-direction, a transport bar 94 for transport in Y-direction and means 95 for transport of pipetting head 92 in Z-direction. Transport system 91 is controlled by control means 96 which may e.g. be part of the control means of an automatic analyzer to which the pipetting unit shown by FIG. 11 belongs. With this pipetting unit, pipetting operations can be effected e.g. on sample or reagent tubes 99 contained in racks 98 of an array 97 of racks.

Materials

With exception of micromechanical pipetting module 11, all other components shown in FIGS. 6 and 7 are made e.g. of chromium steel or other suitable materials. These components can also be made e.g. of aluminum. Cap 42 be made e.g. of chromium steel, aluminum or yellow brass.

The invention claimed is:

1. A pipetting module comprising
   (a) a micromachined pipetting device for pipetting liquid volumes in the submicroliter and microliter range, said micromachined pipetting device including a membrane having a central zone, the central zone of said membrane being displaced by a macroactuator,
   (b) a macroactuator which has an upper end and a lower end for displacing said membrane, and
   (c) means for mechanically coupling said macroactuator to said membrane of said micromachined pipetting device, said coupling means comprising
   (d) a first body for holding the macroactuator, said first body having a side wall having an outer surface and a bottom having an outer surface,
   (e) the macroactuator is mechanically mounted on said first body,
   (f) a second body having an upper outer surface, a lower outer surface, and a bore for receiving said first body, the size of said bore and the size of said first body being such that the outer surface of the side wall of the first body snugly fits within said bore,
   (g) means for fixing the axial position of said first body within said bore comprising
      (i) a first bolt segment and a second bolt segment, said bolt segments being located within said second body, and said bolt segments each having a side wall with the same radius of curvature as a closed line defined by a cross-section of said bore of said second body, and
      (ii) a screw passing through one of the bolt segments and being connectable to the other bolt segment by a screw connection, said screw connection enabling said bolt segments to be pulled against each other in order to reduce the size of a gap existing between said bolt segments and thereby reducing the space available for said first body in said bore of said second body, and
   (h) means for mounting said micromachined device on said second body in such a way that the upper end of the macroactuator exerts a predetermined force or pressure on said membrane of said micromachined device.

2. A pipetting module according to claim 1, wherein the membrane of the micromachined pipetting device is formed by a silicon layer arranged between an upper glass or silicon layer and a lower glass or silicon layer, said lower glass or silicon layer has a bore which provides said macroactuator access to the central zone of said membrane.

3. A pipetting module according to claim 2, wherein said membrane has a boss in its central zone.

4. A pipetting module according to claim 1, wherein said first body has a substantially cylindrical shape and comprises a chamber for receiving said macroactuator, a substantial part of said macroactuator being located in said chamber of said first body.

5. A pipetting module according to claim 1, wherein said closed line is a circle.

6. A pipetting module according to claim 1, wherein said means for mounting said micromachined pipetting device on said second body comprise
   (i) a clamping plate covering the micromachined pipetting device, and
   (ii) a mounting plate located below the micromachined pipetting device and having a window providing said macroactuator access to said membrane, said micromachined pipetting device being arranged between the clamping plate and the mounting plate and being mounted with these plates on said second body.

7. A pipetting module according to claim 1, wherein said micromachined pipetting device is an integrally built device which has an inlet/outlet which may either be connected to a removable pipetting tip or is integrally built with a pipetting tip, said integrally built micromachined pipetting device comprising a micromechanical structure which is integrally built on a silicon wafer and which comprises
   a) a first chamber located within said micromachined pipetting device, the volume comprised within said first chamber may be modified by displacement of the membrane, which is a portion of a wall of said first chamber, said first chamber having an opening, said opening being permanently open and allowing fluid flow into and from an interior of said first chamber,
   b) a channel located within said micromachined pipetting device, said channel establishing a direct, valveless and permanent fluidical connection between said opening of the first chamber and the inlet/outlet of the micromachined pipetting device,
   c) said macroactuator causing a displacement of the central zone of said membrane, and thereby causing aspiration or dispensing of a volume of air or of a liquid into or from said first chamber, which in turn causes aspiration or dispensing of a volume of a liquid sample into or from respectively said pipetting tip.

8. A pipetting module comprising:
   (a) a micromachined pipetting device for pipetting liquid volumes in the submicroliter and microliter range, said micromachined pipetting device including a membrane having a central zone, the central zone of said membrane being displaced by a macroactuator,
   (b) a macroactuator which has an upper end and a lower end for displacing said membrane, and
   (c) means for mechanically coupling said macroactuator to said membrane of said micromachined pipetting device, said coupling means comprising
   (d) a first body for holding the macroactuator, said first body having a side wall having an outer surface and a bottom having an outer surface,
   (e) the macroactuator is mechanically mounted on said first body,
   (f) a second body having an upper outer surface, a lower outer surface, and a bore for receiving said first body, the size of said bore and the size of said first body being such that the outer surface of the side wall of the first body snugly fits within said bore,
   (g) a screw arrangement for fixing the axial position of said first body within said bore, the screw arrangement comprising
      (i) a first bolt segment and a second bolt segment, said bolt segments being located within said second body and said bolt segments each having a side wall with the same radius of curvature as a closed line defined by a cross-section of said bore of said second body and (ii) a screw passing through one of the bolt segments and being connectable to the other bolt segment by a screw connection, said screw connection enabling said bolt segments to be pulled against each other in order to reduce the size of a gap existing between said bolt segments and thereby reducing the space available for said first body in said bore of said second body, and (h) a plate arrangement for mounting said micromachined device on said second body in such a way that the upper end of the macroactuator exerts a predetermined force or pressure on said membrane of said micromachined device.

9. A pipetting module according to claim 8, wherein said membrane of the micromachined pipetting device is formed by a silicon layer arranged between an upper glass or silicon layer and a lower glass or silicon layer, said lower glass or silicon layer has a bore which provides said macroactuator access to the central zone of said membrane.

10. A pipetting module according to claim 9, wherein said membrane has a boss in its central zone.

11. A pipetting module according to claim 8, wherein said first body has a substantially cylindrical shape and comprises a chamber for receiving said macroactuator, a substantial part of said macroactuator being located in said chamber of said first body.

12. A pipetting module according to claim 8, wherein said closed line is a circle.

13. A pipetting module according to claim 8, wherein said plate arrangement for mounting said micromachined pipetting device on said second body comprises (i) a clamping plate covering the micromachined pipetting device, and (ii) a mounting plate located below the micromachined pipetting device and having a window providing said macroactuator access to said membrane, said micromachined pipetting device being arranged between the clamping plate and the mounting plate and being mounted with these plates on said second body.

14. A pipetting module according to claim 8, wherein said micromachined pipetting device is an integrally built device which has an inlet/outlet which may either be connected to a removable pipetting tip or is integrally built with a pipetting tip, said integrally built micromachined pipetting device comprising a micromechanical structure which is integrally built on a silicon wafer and which comprises a) a first chamber located within said micromachined pipetting device, the volume comprised within said first chamber may be modified by displacement of the membrane, which is a portion of a wall of said first chamber, said first chamber having an opening, said opening being permanently open and allowing fluid flow into and from a interior of said first chamber, b) a channel located within said micromachined pipetting device, said channel establishing a direct, valveless and permanent fluidical connection between said opening of the first chamber and the inlet/outlet of the micromachined pipetting device, c) said macroactuator causing a displacement of the central zone of said membrane, and thereby causing aspiration or dispensing of a volume of air or of a liquid into or from said first chamber, which in turn causes aspiration or dispensing of a volume of a liquid sample into or from respectively said pipetting tip.

* * * * *